(12) United States Patent
Asprion (10) Patent No.: US 10,793,494 B2
(45) Date of Patent: Oct. 6, 2020

(54) METHOD FOR SEPARATING MATERIALS BY MEANS OF AN EXTRACTIVE DISTILLATION PROCESS

(71) Applicant: BASF SE, Ludwigshafen am Rhein (DE)

(72) Inventor: Norbert Asprion, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 7 days.

(21) Appl. No.: 16/072,695

(22) PCT Filed: Feb. 2, 2017

(86) PCT No.: PCT/EP2017/052215
§ 371 (c)(1),
(2) Date: Jul. 25, 2018

(87) PCT Pub. No.: WO2017/134143
PCT Pub. Date: Aug. 10, 2017

(65) Prior Publication Data
US 2019/0031581 A1    Jan. 31, 2019

(30) Foreign Application Priority Data

Feb. 5, 2016    (EP) .................................... 16154499

(51) Int. Cl.
*C07C 7/08*        (2006.01)
*B01D 3/00*        (2006.01)
(Continued)

(52) U.S. Cl.
CPC ............... *C07C 7/08* (2013.01); *B01D 3/007* (2013.01); *B01D 3/143* (2013.01); *B01D 3/322* (2013.01);
(Continued)

(58) Field of Classification Search
None
See application file for complete search history.

(56) References Cited

U.S. PATENT DOCUMENTS 4,447,318 A     5/1984  Ogura et al.
6,048,441 A *   4/2000  Auer ...................... B01D 3/148
                                                    159/6.2
(Continued)

FOREIGN PATENT DOCUMENTS

DE    22 08 195 A1    9/1973
EP    0 366 019 A1    5/1990

OTHER PUBLICATIONS

International Search Report dated Apr. 21, 2017, in PCT/EP2017/052215 filed Feb. 2, 2017.

*Primary Examiner* — Derek N Mueller
(74) *Attorney, Agent, or Firm* — Oblon, McClelland, Maier & Neustadt, L.L.P.

(57) ABSTRACT

A method for separating a mixture of materials A and B by extractive distillation, using an extraction medium having a higher affinity to B than to A, collecting a liquid fraction on a collecting tray and heated and partially evaporated in a first indirect heat exchanger, collecting the resultant vapor is released into the column and a non-evaporated proportion of the liquid fraction in the sump of the column, and a series of heating, separation and cooling where partially cooled extraction medium fraction is used as heating medium for a heat exchanger.

12 Claims, 11 Drawing Sheets

(51) Int. Cl.
*B01D 3/14* (2006.01)
*B01D 3/32* (2006.01)
*B01D 3/40* (2006.01)
*C07C 67/54* (2006.01)
*C07C 17/386* (2006.01)
*C01B 7/07* (2006.01)
*C07C 29/84* (2006.01)
*C07C 45/83* (2006.01)
*C07C 253/34* (2006.01)
*C07D 307/08* (2006.01)
*C07C 7/00* (2006.01)
*C07C 9/10* (2006.01)
*C07C 11/08* (2006.01)
*C07C 11/16* (2006.01)

(52) U.S. Cl.
CPC .............. *B01D 3/40* (2013.01); *C01B 7/0712* (2013.01); *C07C 7/005* (2013.01); *C07C 17/386* (2013.01); *C07C 29/84* (2013.01); *C07C 45/83* (2013.01); *C07C 67/54* (2013.01); *C07C 253/34* (2013.01); *C07D 307/08* (2013.01); *C07C 9/10* (2013.01); *C07C 11/08* (2013.01); *C07C 11/16* (2013.01)

(56) References Cited

U.S. PATENT DOCUMENTS

2014/0124358 A1  5/2014  Schwint et al.
2016/0303489 A1  10/2016  Schwint et al.

\* cited by examiner

METHOD FOR SEPARATING MATERIALS BY MEANS OF AN EXTRACTIVE DISTILLATION PROCESS

The invention relates to a method for separating materials by extractive distillation.

It is known that azeotropic or narrow-boiling mixtures that are inseparable or difficult to separate by customary distillation may frequently be separated by an extractive distillation.

In the extractive distillation, the vapors are brought into contact with an extraction medium that selectively decreases the volatility of one of the components of the mixture that is to be separated. The extraction medium has a higher boiling point, or a markedly lower vapor pressure, than the materials that are to be separated. The extraction medium is taken off via the sump of the column, together with one of the materials that are to be separated. The extracted material can be liberated in a stripper and the regenerated extraction medium that is taken off from the sump of the stripper can be reused.

Since methods for separating materials by extractive distillation comprise a plurality of distillations and are therefore energy-intense, an optimum energy integration is important for economic operation thereof. It is known to recover the thermal energy of the regenerated extraction medium to heat the extractive distillation column or to preheat the loaded extraction medium stream. For instance, US 2014/0124358 A1 describes a method in which the extractive distillation column is heated up in a multistage manner via evaporators mounted laterally on the column. Each evaporator warms a side takeoff from the column collecting tray. The liquid/vaporous-mixed-phase stream from the evaporators is recirculated to the extractive distillation column. The column sump is additionally heated via an optional evaporator. The evaporators that are mounted laterally on the column are operated with hot regenerated extraction medium. The optional sump evaporator can additionally be operated with low-pressure steam or medium-pressure steam.

The method of US 2014/0124358 A1 has the disadvantage that the compartments that are arranged one above the other delimited by collecting trays increase the height of the extractive distillation column. Thus, at least compartments arranged one above the other are required if heating of the column via at least three evaporators is to proceed.

The object of the invention is to specify an extractive distillation method that permits optimum energy integration without significant increase of the height of the extractive distillation column.

The object is achieved by a method for separating a mixture of materials A and B by extractive distillation, using an extraction medium having a higher affinity to B than to A, wherein a) a feed stream comprising A and B is conducted towards the extraction medium in a column, wherein an overhead fraction comprising A and also a liquid fraction comprising B and extraction medium are obtained,
b) the liquid fraction is collected on a collecting tray and heated and partially evaporated in a first indirect heat exchanger, the resultant vapor is released into the column and a non-evaporated proportion of the liquid fraction is collected as sump fraction in the sump of the column,
c) the sump fraction is successively heated in a second indirect heat exchanger and a third indirect heat exchanger and in part evaporated, wherein the resultant vapor is at least in part released into the column,
d) the sump fraction is separated in a stripper into a fraction comprising B and an extraction medium fraction,
e) the extraction medium fraction is used as heating medium for the second heat exchanger, wherein a partially cooled extraction medium fraction is obtained, and an external heating medium is used for the third heat exchanger, and
f) the partially cooled extraction medium fraction is used as heating medium for the first heat exchanger.

According to the invention, the sump fraction is successively heated in a second indirect heat exchanger and a third indirect heat exchanger and in part evaporated. The resultant vapor is at least in part released into the column, preferably into the volume above the column sump. Owing to the double heat transfer, in which the sump fraction is first heated by means of the extraction medium fraction originating from the stripper and then by means of an external heating medium, the thermal energy of the regenerated extraction medium fraction is optimally utilized. The external heating medium delivers only the energy input required in order to elevate the sump temperature from the temperature level which is reached by heating with the regenerated extraction medium fraction, to a desired value. In addition, liquid fraction is collected on a collecting tray and heated and in part evaporated in a first indirect exchanger. Owing to the lower temperature of the internal material stream in comparison with the sump temperature of the column, for the intermediate heating, heat energy at a low temperature level can be used. According to the invention, partly cooled extraction medium fraction can be used as heating medium for the first heat exchanger.

The feed stream comprising A and B is conducted towards the extraction medium in a column. The feed stream comprising A and B is introduced into a lower region or a central region of the column. The extraction medium is introduced at the top or into an upper region of the column. The extraction medium is introduced in the liquid state into the column. The feed stream can be introduced into the column in the vaporous or liquid state.

As separating-effecting internals, the column preferably comprises trays, random packings and/or structured packings. The column can have, e.g., an enrichment zone situated above the feed pipe of the feed stream comprising A and B, and a stripping zone situated beneath the feed pipe of the feed stream.

An overhead fraction comprising A and a liquid fraction comprising B and extraction medium are obtained.

In the overhead fraction comprising A, the amount-of-substance fraction A/(A+B) is higher, preferably at least 1.3 times higher, in particular at least 1.5 times higher, than in the feed stream comprising A and B. The amount-of-substance fraction A/(A+B) is calculated by dividing the amount of substance A by the sum of the amount of substance A and the amount of substance B. The overhead fraction comprising A is conducted out of the column at the top of the column.

The liquid fraction comprising B and extraction medium is collected on a collecting tray. The collecting tray is arranged in the column above the column sump, for example between the sump and the stripping zone. The collected liquid fraction is heated and in part evaporated in a first indirect heat exchanger. The first heat exchanger is arranged preferably outside the column. The liquid fraction can be taken off from the collecting tray and conducted into the heat exchanger arranged outside the column.

The vapor formed on the heating in the first heat exchanger is released into the column and a non-evaporated proportion of the liquid fraction is collected as sump fraction in the sump of the column. Generally, a liquid/vaporous-mixed-phase stream from the evaporator which comprises the resultant vapor and the non-evaporated proportion of the liquid fraction, is recirculated into the column beneath the collecting tray. The resultant vapor can also be separated from the non-evaporated proportion of the liquid fraction, e.g. in a phase separator, and both phases can be conducted separately into the column.

In the method according to the invention, any form of indirect heat exchanger suitable for transferring heat from a liquid to another liquid can be used as first heat exchanger. The first heat exchanger can be, e.g., a falling-film evaporator, a kettle evaporator, a forced-circulation evaporator, or a natural-circulation evaporator. Preferably, the first heat exchanger is a natural-circulation evaporator.

The method according to the invention has the advantage that the first heat exchanger can be operated even at very low boil-off rates, that is to say even with low heat supply, as a natural-circulation evaporator, that is to say without additional costs and energy expenditure for a pump. This is due to the difference in height generally existing between the first heat exchanger and the collecting tray situated further above, and also to the static pressure of the projecting liquid column. As a result, even at a low boil-off rate (that is to say even with low heat supply), a continuous passage through the first heat exchanger can be ensured, without the risk that the circulation comes to a standstill. Preferably, the first heat exchanger is arranged outside the column far enough below that the non-evaporated proportion of the liquid fraction obtained from the first heat exchanger occurs beneath the collecting tray, preferably in a range from 0.15 m to 0.70 m beneath the collecting tray, particularly preferably in a range from 0.20 m to 0.60 m beneath the collecting tray, very particularly preferably in a range from 0.25 m to 0.50 m beneath the collecting tray. For example, the first heat exchanger can be arranged outside the column far enough below that the outlet thereof for the non-evaporated proportion of the liquid fraction or for the liquid/vaporous-mixed-feed stream which comprises the resultant vapor and the non-evaporated proportion of the liquid fraction, is situated beneath the collecting tray, preferably in a range from 0.15 m to 0.70 m beneath the collecting tray, particularly preferably in a range from 0.20 m to 0.60 m beneath the collecting tray, very particularly preferably in a range from 0.25 m to 0.50 m beneath the collecting tray. This distance relates to the distance between two horizontal planes, wherein the lowest point which the liquid fraction reaches on the collecting tray is in the upper plane and the lowest point of the outlet of the evaporator is in the lower plane. Preferably, the first heat exchanger is not mounted too far below. As a result, this will also contribute to the fact that the height of the extractive distillation column need not be increased. An optimum with respect to costs and energy expenditure on the one hand and column height on the other is thereby achieved.

The sump fraction is successively heated and in part evaporated in a second indirect heat exchanger and a third indirect heat exchanger, where the resultant vapor is at least in part released into the column. This can be performed by releasing the vapor at least in part into the sump and/or into the region between the sump and the collecting tray.

The sump fraction can be conducted successively through the second heat exchanger and the third heat exchanger in various ways, as described hereinafter.

The sump fraction can be circulated via a sump circulation, in which the sump fraction is successively conducted through the second indirect heat exchanger and the third indirect heat exchanger. If the sump fraction is conducted in the one sump circulation successively through the second indirect heat exchanger and the third indirect heat exchanger, the vapor formed in the second heat exchanger is not separated off from the sump fraction before the sump fraction enters the third heat exchanger. Therefore, a liquid/vaporous-mixed-phase stream passes into the third heat exchanger from the second evaporator. In the third heat exchanger, a further proportion of the sump fraction is evaporated.

The sump fraction thus heated can then be conducted through a flow divider, in order to separate off from the sump circulation the sump fraction that is to be fed to the stripper.

The sump fraction, downstream of the third indirect heat exchanger, can be conducted through a cell communicating on the vapor side with the column, in which cell the resultant vapor is separated off from the sump fraction and from which the sump fraction that is to be fed to the stripper is withdrawn. The cell can be integrated into the sump of the column or a phase separator arranged outside the column.

When the cell is integrated into the sump of the column, the vapor-side communication of the cell with the column is preferably achieved in that the cell is open towards the vapor situated above the sump of the column.

When the cell is a phase separator arranged outside the column, the vapor-side communication of the cell with the column is preferably achieved in that the phase separator is connected to the column via a line, via which vapor can escape from the phase separator into the column. Preferably, the line opens out into the column above the surface of the sump fraction collecting in the sump.

From the cell, through which the circulated sump fraction is conducted downstream of the third indirect heat exchanger, a part of the sump fraction is recirculated to the sump of the column. When the cell is integrated into the sump of the column, this can be achieved in that a part of the sump fraction conducted through the cell is allowed to overflow into the (remaining) sump of the column. When the cell is a phase separator arranged outside the column, a part of the sump fraction can be recirculated from the cell into the sump of the column, by connecting the phase separator to the column via a line connected to an overflow.

Since a uniform admission flow into the third heat exchanger with a liquid/vaporous-mixed-phase stream from the second evaporator can sometimes be difficult, an intermediate outgassing of the liquid/vaporous-mixed-phase stream is preferred. For instance, the sump fraction can be conducted through three cells communicating on the vapor side with the column, by collecting the sump fraction in a first cell, taking off the sump fraction from the first cell and conducting it through the second heat exchanger into the second cell, taking off the sump fraction from the second cell, and conducting it through the third heat exchanger into the third cell, and taking off from the third cell the sump fraction that is to be fed to the stripper. This has the advantage that vapor formed in the second heat exchanger does not pass into the third heat exchanger, but can outgas directly into the column from the cell communicating on the vapor side with the column. Then, a substantially single-phase liquid sump fraction to which the heat may be transferred better, passes into the third heat exchanger.

The second cell and the third cell can be integrated independently of one another into the sump of the column, or be phase separators arranged outside the column. Both phase separators can be arranged spatially separate from one another, or be arranged in one container. When the second cell and the third cell are phase separators arranged outside the column, the first cell integrated into the sump of the column forms the sump of the column.

In the case of cells integrated into the sump of the column, the vapor-side communication of the cell with the column is preferably achieved in that the respective cell is open to the volume situated over the sump of the column.

In the case of phase separators arranged outside the column, the vapor-side communication of the cell with the column can be achieved in that the phase separator is connected to the column via a line, via which the vapor can escape into the column from the phase separator. Alternatively, the vapor-side communication of the cell with the column can be achieved in that the phase separator is connected via a line to another phase separator which is connected via a line to the column. Preferably, the respective line opens out into the column above the surface of the sump fraction collecting in the sump.

A part of the sump fraction can be recirculated into preceding cells. For example, from the second to the first cell, from the third to the first cell, and/or from the third to the second cell.

For instance, e.g. a part of the sump fraction can be conducted into the column from one or optionally both phase separators, for example in each case via an overflow. The overflow can open out via a line into the preceding phase separator, or into the column. Thus, a part of the sump fraction can be allowed to overflow from the second cell into the first, from the third into the first cell, and/or from the third into the second cell.

In an embodiment of the method according to the invention, the three cells are integrated into the sump of the column.

Regardless of in which manner the sump fraction is successively conducted through the second heat exchanger and the third heat exchanger, any cell integrated into the sump of the column can be separated off from the remaining sump of the column or from one or more other cells integrated into the sump of the column by any suitable liquid-impermeable barrier.

A preferred liquid-impermeable barrier is a dividing wall, in particular a vertical dividing wall. Preferably, the dividing wall comprises metal. The dividing wall can be constructed, in particular, as a concentric cylinder, or as a planar dividing wall that, viewed in the column cross section, is arranged along a circle radius or a circle chord.

Preferably, a part of the sump fraction may be allowed to overflow over the liquid-impermeable barrier from a cell integrated in the sump of the column into the remaining sump of the column, or into a preceding cell.

The sump fraction comprising B and extraction medium is then separated in a stripper into a fraction comprising B and a fraction comprising extraction medium. The stripper is heated, in particular the sump of the stripper, in order to achieve separation into the two fractions. The stripper can be heated, e.g. via a sump circulation. The sump circulation can be heated, for example, via a heat exchanger, in which steam is used as heating medium. The separation into the two fractions in the stripper can be facilitated by stripping and/or pressure reduction.

Preferably, the fraction comprising B is removed at the top of the stripper. In the fraction comprising B, the amount-of-substance fraction B/(A+B) is higher, preferably at least 1.3 times higher, in particular at least 1.5 times higher, than in the feed stream comprising A and B. The amount-of-substance fraction B/(A+B) is calculated by dividing the amount-of-substance B by the sum of the amount-of-substance A and the amount-of-substance B.

Preferably, a regenerated extraction medium fraction is taken off at the sump of the stripper.

The regenerated extraction medium fraction is used as heating medium for the second heat exchanger, wherein a partly cooled extraction medium fraction is obtained. Since a part of the heat from the extraction medium fraction is transferred in the second heat exchanger to the sump fraction, a partial cooling of the extraction medium fraction occurs.

Preferably, the second heat exchanger is dimensioned in such a manner that the temperature of the partially cooled extraction medium fraction exiting from the second heat exchanger is at most 30 K, e.g. 1 to 25 K, in particular 2 to 20 K, preferably 3 to 15 K above the temperature of the sump fraction exiting from the heat exchanger.

For the third heat exchanger, an external heating medium is used. Using the external heating medium, the desired sump temperature is set. The sump fraction entering into the third heat exchanger, owing to the preceding second heat exchanger, is preheated. Therefore, the amount of heat to be additionally supplied to set the desired sump temperature is restricted to a minimum.

In the method according to the invention, any form of indirect heat exchanger that is suitable for transferring heat from a liquid to another liquid can be used as second or third heat exchanger. Both heat exchangers can independently be falling-film evaporators, kettle evaporators, forced-circulation evaporators, or natural-circulation evaporators. Preferably, at least the second or third heat exchanger is a natural-circulation evaporator or a falling-film evaporator. In falling-film evaporators, the residence time of the sump fraction is particularly short, as a result of which a particularly gentle heating or evaporation can be ensured. Therefore, falling-film evaporators are preferably used, in particular in the case of heat-sensitive extraction media. This applies in particular to the third heat exchanger, since the external heating medium used for the third heat exchanger is generally hotter than the heating media used for the first and second heat exchanger.

The partially cooled extraction medium fraction is used as heating medium for the first heat exchanger. For this purpose, the partially cooled extraction medium fraction exiting from the second heat exchanger is conducted through the first heat exchanger.

From the first heat exchanger, a cooled extraction medium fraction is obtained. Preferably, the first heat exchanger is dimensioned in such a manner that the temperature of the cooled extraction medium fraction exiting from the first heat exchanger is at most 30 K, e.g. 1 to 25 K, in particular 2 to 20 K, preferably 3 to 15 K above the temperature of the non-evaporated proportion of the liquid fraction exiting from the heat exchanger.

In order to close the extraction medium circuit, at least a part of the cooled extraction medium fraction obtained from the first indirect heat exchanger is recycled to step a). Before entry into the extractive distillation column, the cooled extraction medium fraction is preferably further cooled.

A and B are vaporizable and condensable or soluble materials, i.e. materials that may be converted from the liquid or dissolved state to the gaseous state, and vice versa.

Preferably, A and B are materials, the boiling temperature of which at standard pressure, that is to say at 1013.25 hPa differs by, e.g., at most 25 K, in particular at most 20 K, preferably at most 15 K, or materials that form an azeotrope.

A can comprise one or more isomers, for example different isomeric butanes, when A is butane.

B can comprise one or more isomers, for example different isomeric butenes, when B is butene, butadiene or mixtures thereof.

The method according to the invention can be a method wherein
i. A is butane and B is butene, butadiene or mixtures thereof, or
ii. A is pentane and B is pentene, isoprene or mixtures thereof, or
iii. A is hexane and B is benzene, or
iv. A is 2-propanol and B is water, or
v. A is hydrogen chloride and B is water, or
vi. A is acetonitrile and B is water, or
vii. A is 2-butyl acetate and B is 2-butanol, or
viii. A is tetrahydrofuran and B is methanol, or
ix. A is acetone and B is chloroform, or
x. A is ethanol and B is water, or
xi. A is acetone and B is methanol, or
xii. A is a mixture of ethanol and water and B is ethyl acetate.

In the method according to the invention, the extraction medium has a higher affinity to B than to A. That is to say that the extraction medium forms stronger interactions with B than with A. The affinity of the extraction medium to A and to B can be determined by those skilled in the art, e.g., in that they determine the solubility of A or B in the extraction medium. For example, they can stir one aliquot each of extraction medium under an atmosphere of A and an atmosphere of B and determine how much of A or of B has dissolved in the extraction medium.

Generally, the boiling temperature of the extraction medium under standard conditions is higher by at least 40 K, in particular at least 50 K, preferably at least 60 K, particularly preferably at least 80 K than the boiling temperatures of both substances A and B under standard conditions.

Depending on the materials A and B cited above under i. to xiii., in part, different extraction media are preferred, wherein the preferred extraction medium in the case of
i. is selected from dimethylformamide, N-methylpyrrolidone, acetonitrile, furfural and dimethyl sulfoxide,
ii. is selected from dimethylformamide and N-methylpyrrolidone,
iii. is selected from phenol, N-methylpyrrolidone and N-formylmorpholine,
iv. is a solution of calcium chloride in water, or is selected from dimethyl sulfoxide and ethylene glycol,
v. is sulfuric acid,
vi. is ethylene glycol,
vii. is N,N-dimethylacetamide,
viii. is water,
ix. is dimethyl sulfoxide,
x. is selected from ethylene glycol, glycerol and dimethyl sulfoxide,
xi. is water,
xii. is selected from dimethyl sulfoxide, glycerol and diethylene glycol, 1-naphthol, hydroquinone and dimethylformamide.

In a particularly preferred embodiment of the method according to the invention, A is butane and B is butene, butadiene or mixtures thereof, and the extraction medium comprises N-methylpyrrolidone. Preferably, the feed stream comprises butane, butene and/or butadiene, N-methylpyrrolidone and water, and the extraction medium comprises 80 to 97% by weight N-methylpyrrolidone and 3 to 20% by weight water.

A feed stream containing butane, butene and butadiene is obtained, for example, by catalytic dehydrogenation of n-butane. It can be a non-oxidative, catalytic dehydrogenation, or an oxidative catalytic dehydrogenation. The resultant mixtures, in addition to butane, butane and butadiene, generally comprise inert gases such as hydrogen, nitrogen and/or carbon dioxide. The inert gases can be separated off by absorption of the butene and/or butadiene, butane, hydrogen and/or nitrogen and optionally carbon-dioxide-containing material stream in an absorption medium and subsequent desorption of butene, butadiene and butane.

In an embodiment, as absorption medium, a solvent or solvent mixture is used which is used as extraction medium in the subsequent extractive distillation. The absorption medium preferably comprises 80 to 97% by weight N-methylpyrrolidone and 3 to 20% by weight water. The absorption medium that is loaded with butene, butadiene and butane is passed as feed stream into the extractive distillation. A feed stream comprising butane, butene and/or butadiene is formed, bringing a fluid comprising butane, butene and/or butadiene and hydrogen and/or nitrogen into contact with the liquid absorption medium in an absorption column. The fluid can be conducted into a lower region of an absorption column and the absorption medium can be conducted into an upper region of the absorption column, wherein a water-comprising overhead stream is obtained at the top of the absorption column and the feed stream is obtained from the sump of the absorption column.

The absorption medium and the extraction medium can be formed by dividing the cooled extraction medium fraction obtained from the first indirect heat exchanger, for example by conducting the extraction medium fraction exiting from the first indirect heat exchanger through a flow divider in which the extraction medium fraction is divided into an extraction medium stream and an absorption medium stream. Further cooling can proceed both upstream of the flow divider, and also downstream of the flow divider.

The invention will be illustrated in more detail by the accompanying drawings.

Figure 1:
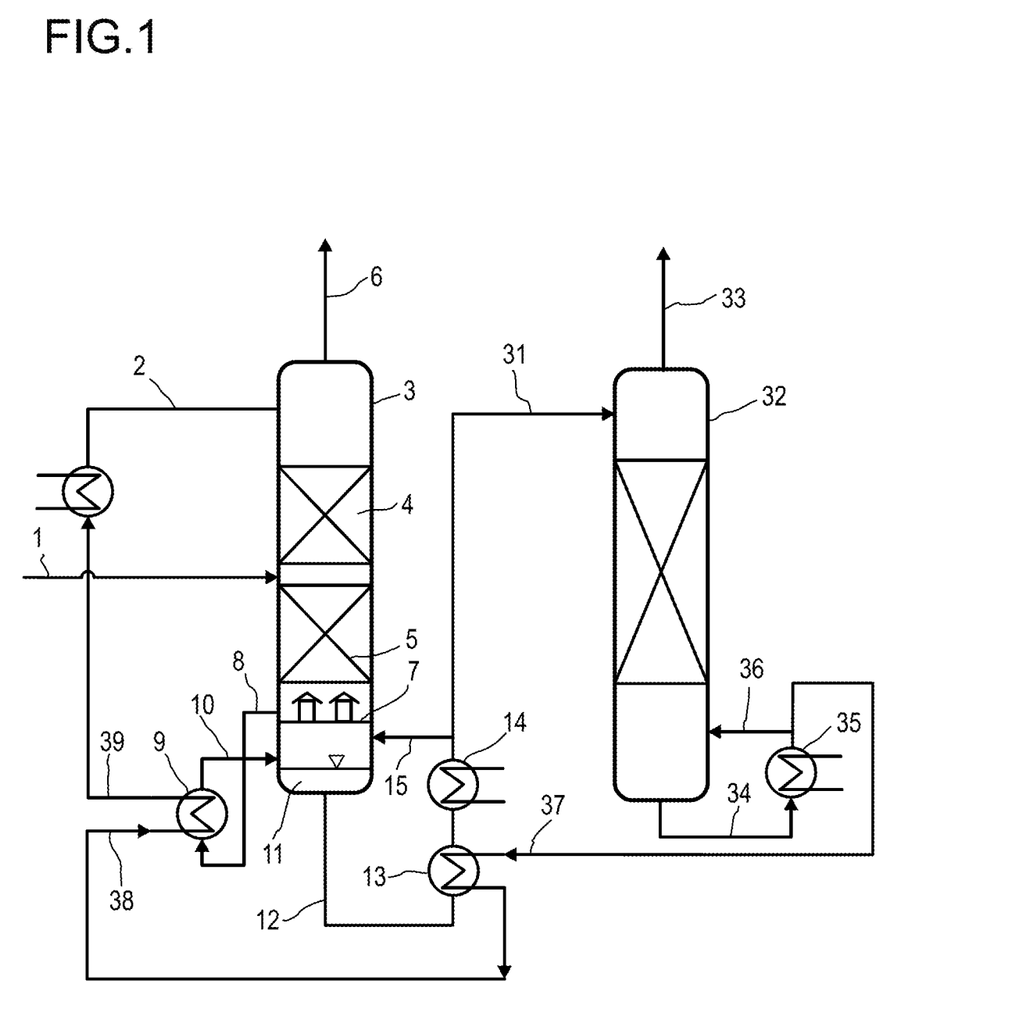
FIG. 1 shows schematically an installation for carrying out a method according to the invention.

In the installation shown in FIG. 1, the feed stream 1 comprising A and B is conducted towards extraction medium fed via line 2 in the column 3, by conducting the feed stream 1 between the enrichment zone 4 and the stripping zone 5 into the column 3 and the extraction medium 2 into the column 3 above the enrichment zone 4. In this case, the overhead fraction 6 comprising A and also the liquid fraction comprising B and extraction medium are obtained. The liquid fraction is collected on the collecting tray 7. The liquid fraction is conducted via line 8 into the first indirect heat exchanger 9 in which it is heated and partially vaporized. In the first heat exchanger 9, a two-phase mixture forms that comprises the resultant vapor and the non-evaporated proportion of the liquid fraction. The two-phase mixture is recirculated via line 10 into the region of the column 3 situated between the sump and the collecting tray 7. Non-evaporated liquid fraction collects as sump fraction 11 in the sump of the column 3. The sump fraction 11 is heated and in part evaporated successively in a second indirect heat exchanger 13 and a third indirect heat exchanger 14. For this purpose the sump fraction 11 is circulated via a sump circulation in which the sump fraction is taken off via line 12 from the sump of the column, and is conducted successively through the second indirect heat exchanger 13 and the third indirect heat exchanger 14 and via line 15. Via line 31, a part of the circulating sump fraction is conducted into the stripper 32 and divided therein into a fraction 33 that comprises B discharged at the top of the stripper, and an extraction medium fraction. The sump of the stripper is heated via a sump circuit (34, 35, 36), via which the extraction medium fraction is circulated, and in which it is heated via a heat exchanger 35. The extraction medium fraction is used as heating medium for the second heat exchanger by conducting it via line 37 and through the second heat exchanger 13. In this case a partially cooled extraction medium fraction is obtained. For the third heat exchanger 14, an external heating medium is used. The partially cooled extraction medium fraction is used as heating medium for the first heat exchanger, by conducting it via line 38 and through the first heat exchanger 9. The cooled extraction medium fraction obtained from the first heat exchanger 9 is recycled after further cooling, by conducting into cooler 40 via line 39 the cooled extraction medium fraction exiting from the first heat exchanger, in order to form the extraction medium that is fed via line 2.

The embodiments of column 3 that are shown in FIGS. 2 to 7 permit a procedure, wherein the sump fraction is conducted through three cells communicating on the vapor side with the column, by collecting the sump fraction in a first cell integrated into the sump of the column, taking off the sump fraction from the first cell and conducting it through the second heat exchanger into the second cell, taking off the sump fraction from the second cell and conducting it through the third heat exchanger into the third cell and taking off from the third cell the sump fraction that is to be fed to the stripper.

Figure 2:
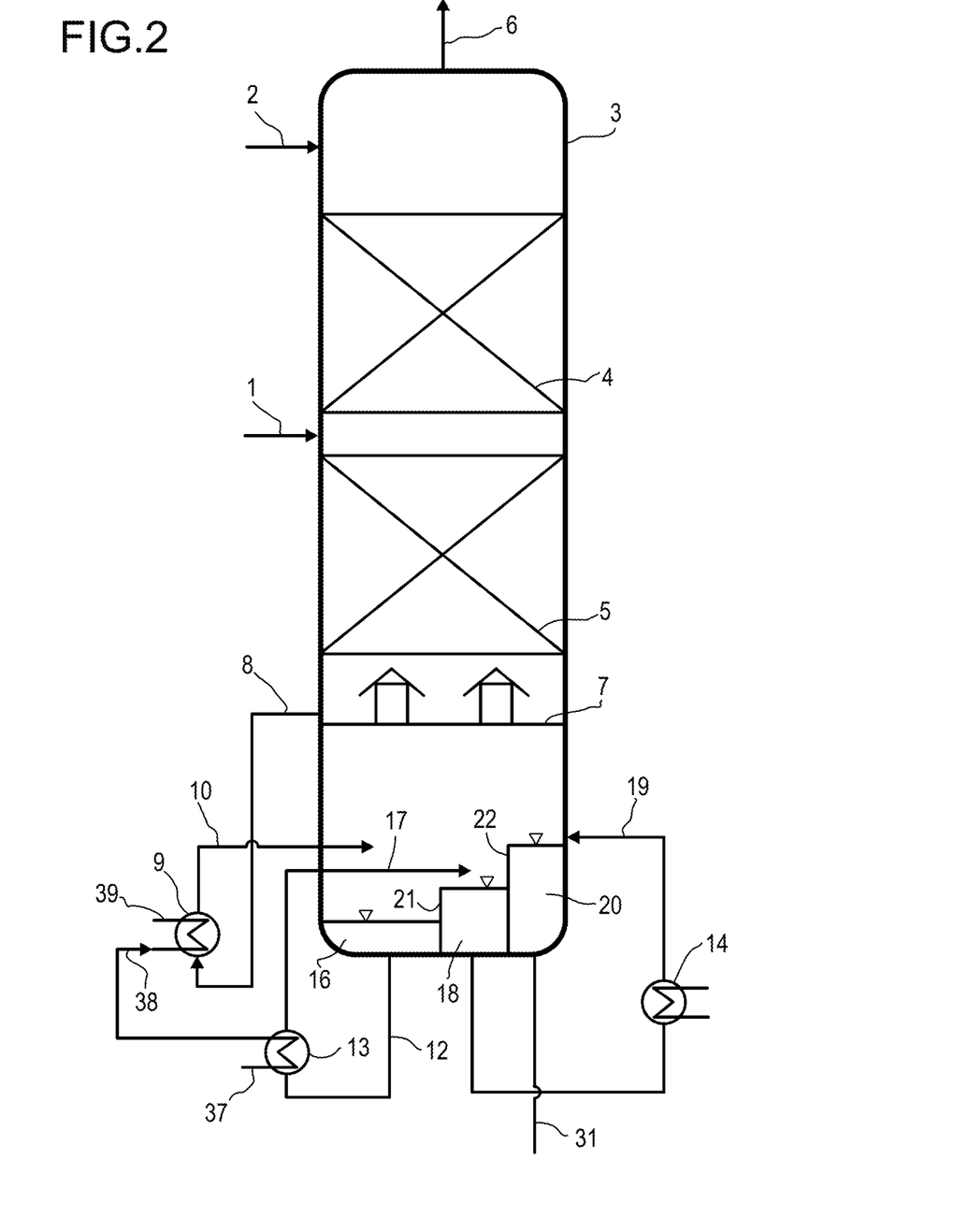
FIG. 2 shows schematically certain embodiments of the column 3 shown in FIG. 1.

In the embodiment of column 3 shown in FIG. 2, all three cells are integrated into the sump of the column. Line 10 opens out above the first cell 16. The two-phase mixture formed in the first heat exchanger 9 from the liquid fraction is conducted via line 10 into the region situated between the sump and the collecting tray 7 above the first cell 16, in such a manner that the non-evaporated proportion of the liquid fraction collects as sump fraction in the first cell 16 and the resultant vapor is released into the column 3. The sump fraction is taken off via line 12 from the first cell 16 and it is conducted via the second heat exchanger 13 and via line 17 into the region above the second cell 18 situated between the sump and the collecting tray, in such a manner that the non-evaporated proportion of the sump fraction collects in the second cell 18 and the resultant vapor is released into the column 3. The first cell 16 is separated off from the second cell 18 by a dividing wall 21. The sump fraction is taken off from the second cell 18 and conducted through the third heat exchanger 14 and via line 19 into the region above the third cell 20 situated between the sump and the collecting tray in such a manner that the non-evaporated proportion of the sump fraction collects in the third cell 20 and the resultant vapor is released into the column 3. The second cell 18 is separated off from the third cell 20 by a dividing wall 22. The sump fraction that is to be fed to the stripper via line 31 is taken off from the third cell. When more sump fraction is fed to the third cell 20 via line 19 than is taken off via line 31, the sump fraction can overflow from the third cell 20 over the dividing wall 22 into the second cell 18. When more sump fraction is fed to the second cell 18 via line 17 than is taken off from the second cell 18, the sump fraction can overflow from the second cell 18 over the dividing wall 20 into the first cell 16.

Figure 2A:
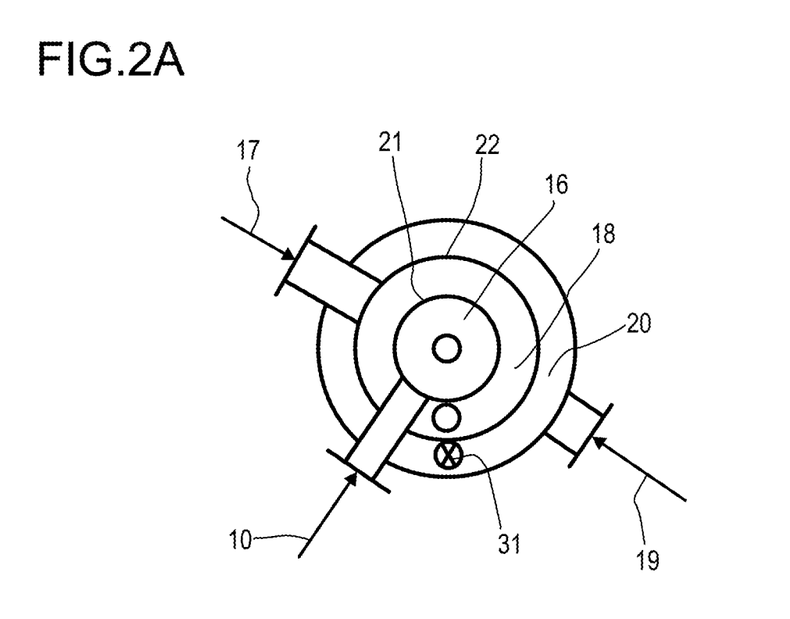
FIGS. 2A-2C show in each case preferred arrangements for the dividing walls for dividing the sump of the column of FIG. 2.
Figure 2B:
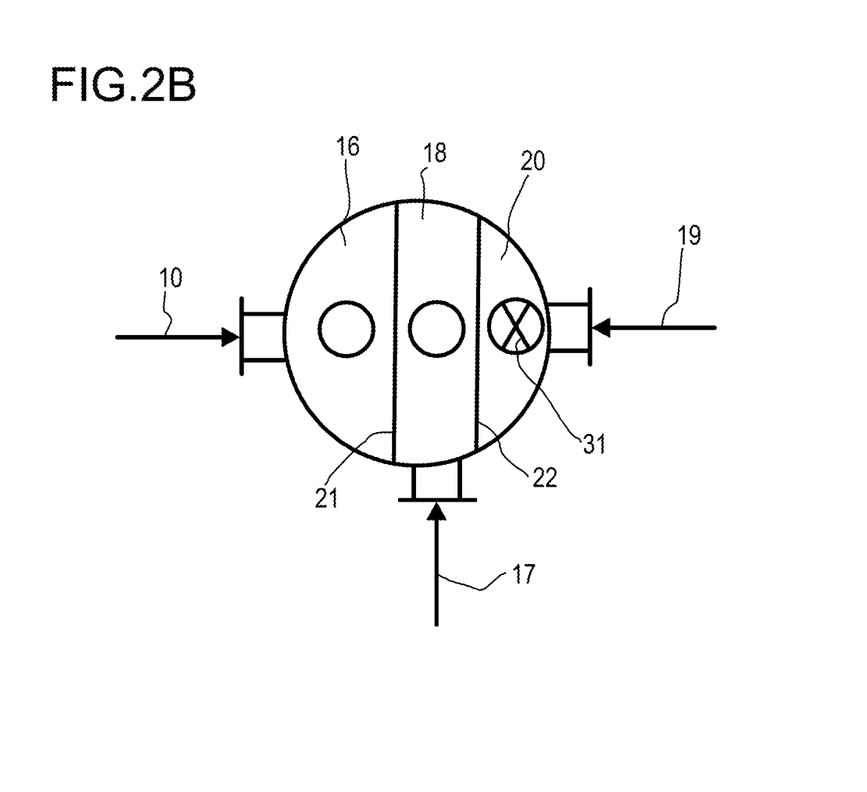
Figure 2C:
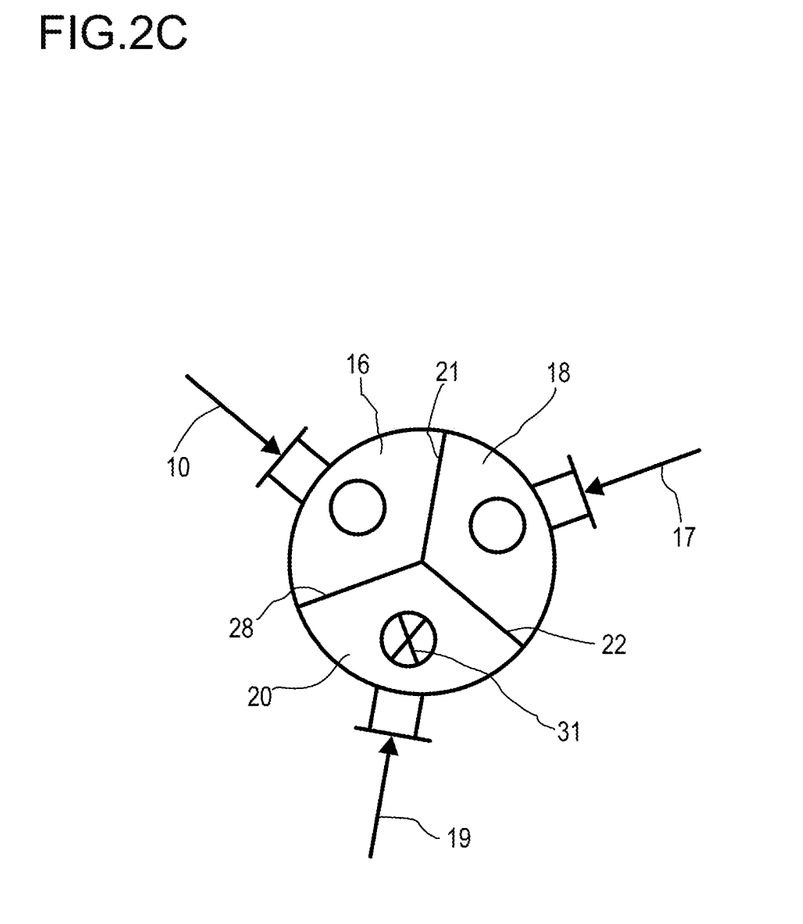

The cross-sectional views in FIGS. 2A-2C each show preferred arrangements of the dividing walls for dividing the column sump into the three cells 16, 18 and 20: a concentric arrangement of the dividing walls in FIG. 2A, an arrangement in the form of chords of a circle in FIG. 2B, and in the form of radii of a circle in FIG. 2C.

Figure 3:
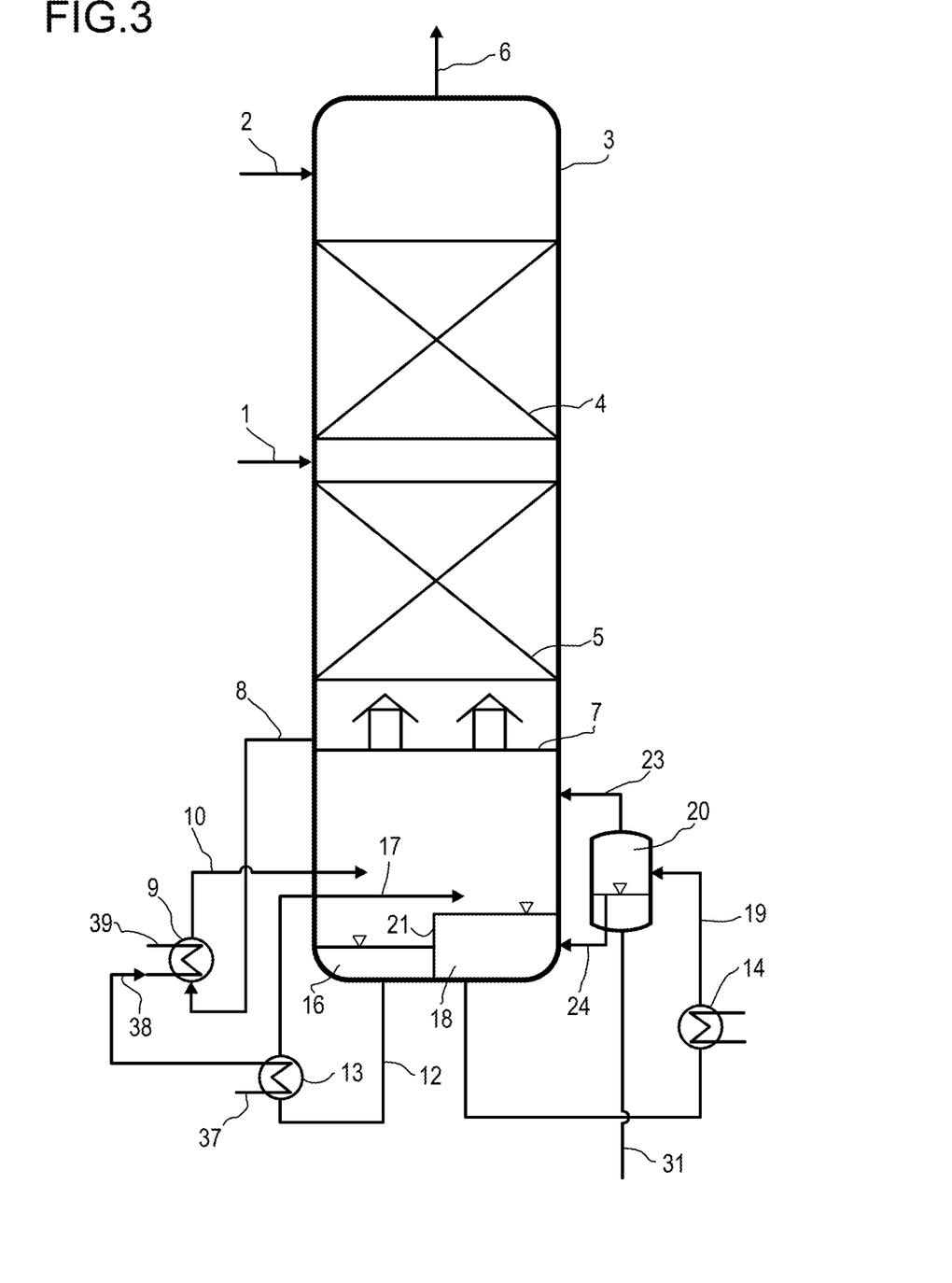
FIGS. 3 to 9 show schematically further embodiments of the column 3 shown in FIG. 1.

In the embodiment of column 3 shown in FIG. 3, the first cell 16 and the second cell 18 are integrated into the sump of the column. The third cell 20 is a phase separator arranged outside the column. Line 10 opens out above the first cell 16. The two-phase mixture formed from the liquid fraction in the first heat exchanger 9 is conducted via line 10 into the region above the first cell 16 situated between the sump and the collecting tray 7, in such a manner that the non-evaporated proportion of the liquid fraction is collected as sump fraction in the first cell 16 and the resultant vapor is released into the column 3. The sump fraction is taken off from the first cell 16 via line 12 and is conducted through the second heat exchanger 13 and via line 17 into the region above the second cell 18 situated between the sump and the collecting tray, in such a manner that the non-evaporated proportion of the sump fraction collects in the second cell 18 and the resultant vapor is released into the column 3. The first cell 16 is separated off from the second cell 18 by a dividing wall 21. The sump fraction is taken off from the second cell 18 and it is conducted through the third heat exchanger 14 and via line 19 into the phase separator. The phase separator has an overflow which opens out into line 24. Via the overflow, sump fraction is allowed to overflow from the phase separator into the second cell 18. The overflow introduced into the phase separator which is fed via line 24, submerged, into the column in this case acts like a siphon and prevents the phase separator from running empty provided that line 19 conducts more liquid than line 31. The vapor collecting in the phase separator is released into the column via line 23. The sump fraction that is to be fed to the stripper via line 31 is taken off from the phase separator.

Figure 4:
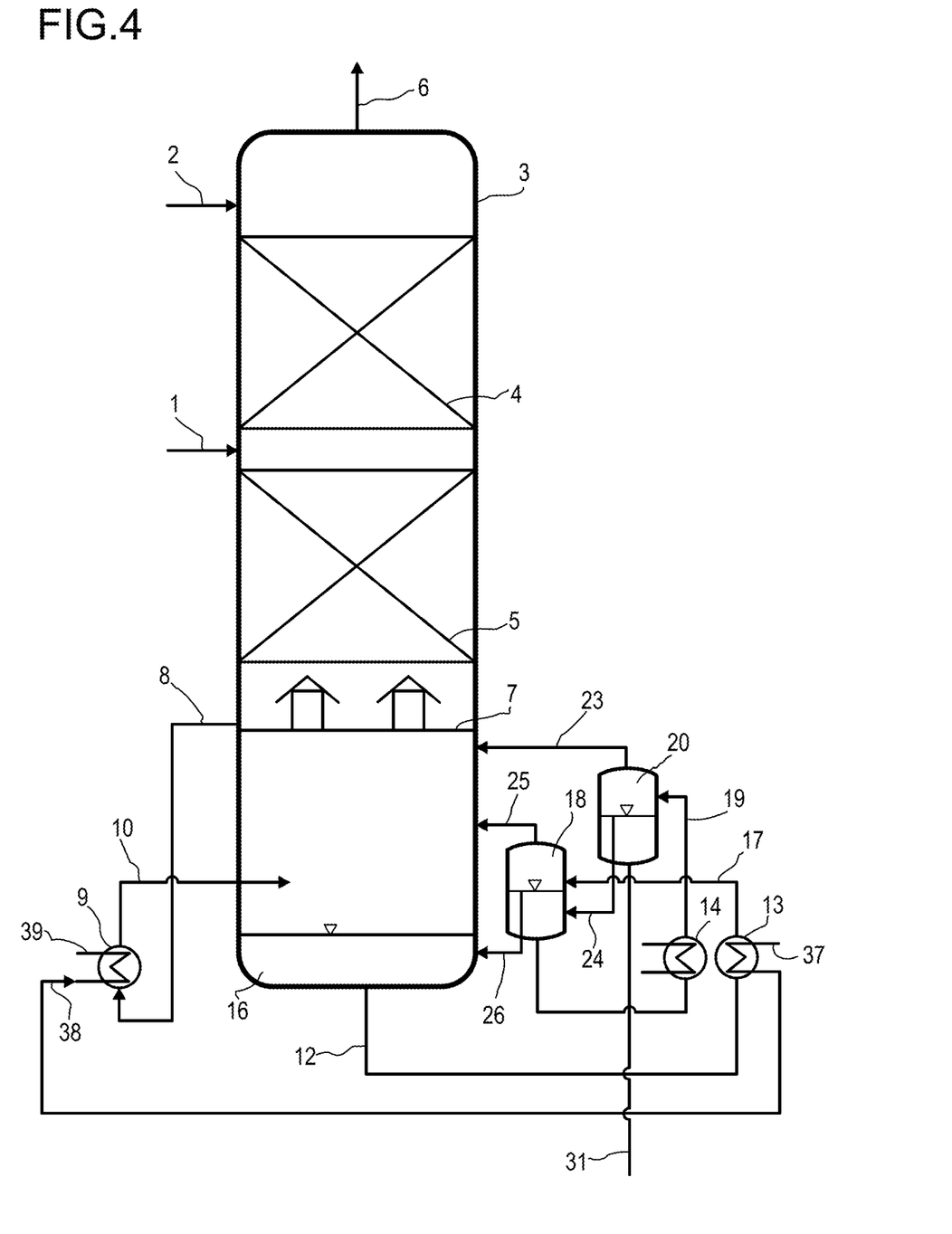

In the embodiment of column 3 shown in FIG. 4, the second cell 18 and the third cell 20 are each phase separators arranged outside the column. The non-evaporated proportion of the liquid fraction is collected as sump fraction in the first cell 16 that is integrated into the sump of the column. The sump fraction is taken off from the first cell 16 via line 12 and is conducted through the second heat exchanger 13 and via line 17 into the phase separator 18. The sump fraction is taken off therefrom and is conducted through the third heat exchanger 14 and via line 19 into the phase separator 20. The phase separators each have an overflow, via which sump fraction is allowed to overflow via line 26 from the phase separator 18 into the first cell 16 and also via line 24 from the first separator 20 into the phase separator 18. The vapors collecting in the phase separators are released via lines 23 and 25 into the column. The sump fraction that is to be fed to the stripper via line 31 is taken off from the phase separator 20.

Figure 5:
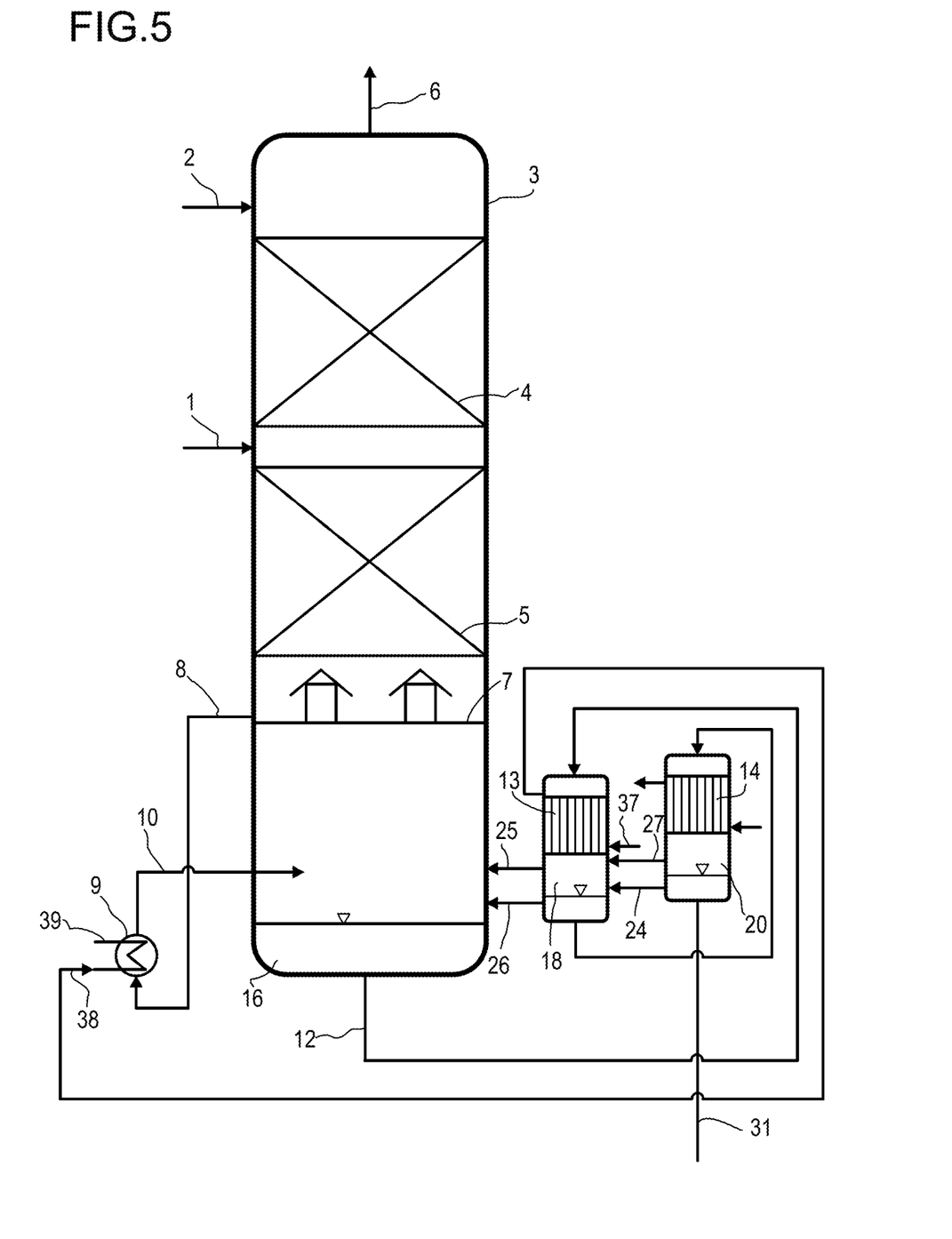

In the embodiment of column 3 shown in FIG. 5, the second cell 18 and the third cell 20 are each phase separators arranged outside the column. The second and third heat exchangers 13 and 14 are integrated into the upper region of the phase separators 18 and 20. The sump fraction is taken off via line 12 from the first cell 16, conducted into the phase separator 18 and therein through the second heat exchanger 13. The sump fraction is taken off from the second cell 18, conducted into the phase separator 20 and therein through the third heat exchanger 14. Both heat exchangers are falling-film evaporators through which the sump fraction flows from top to bottom. Via line 25, sump fraction is conducted from the phase separator 20 into the phase separator 18. Sump fraction from the phase separator 18 is conducted into the first cell 16 via line 26. The vapor collecting in the phase separator 18 is released into the column via line 25. The vapor collecting in the phase separator 20 is conducted via line 25 into the phase separator 18. The sump fraction to be fed to the stripper via line 31 is taken off from the phase separator 20.

Figure 6:
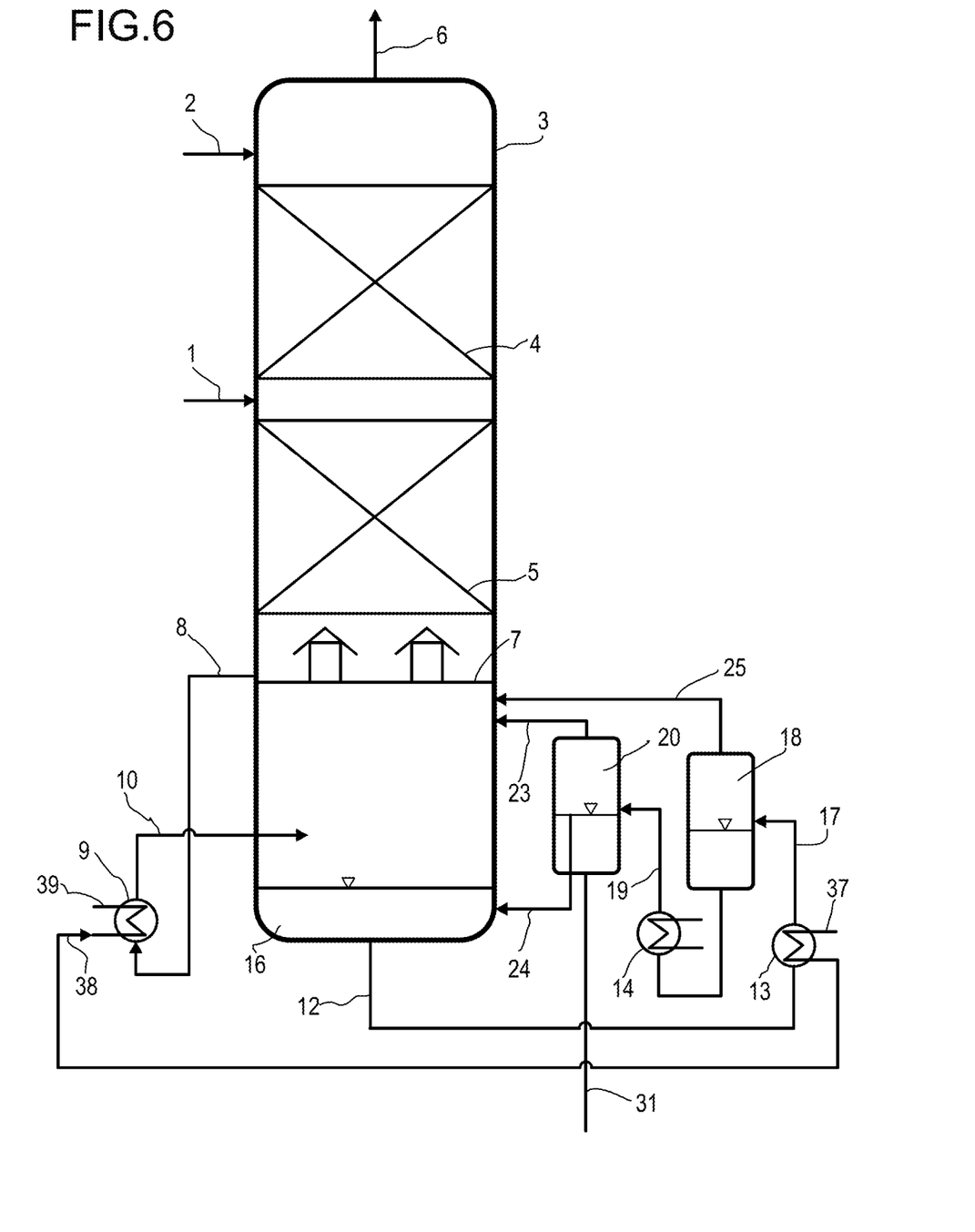

In the embodiment of column 3 shown in FIG. 6, the second cell 18 and the third cell 20 are each phase separators arranged outside the column. The non-evaporated proportion of the liquid fraction is collected as sump fraction in the first cell 16 that is integrated into the sump of the column. The sump fraction is taken off via line 12 from the first cell 16 and it is conducted through the second heat exchanger 13 and via line 17 into the phase separator 18. The sump fraction is taken off from the second cell 18 and conducted through the third heat exchanger 14 and via line 19 into the phase separator 20. The phase separator 20 has an overflow, via which the sump fraction is allowed to overflow via line 24 into the first cell 16. The vapors collecting in the phase separators are released into the column via lines 23 and 25. The sump fraction to be fed to the stripper via line 31 is taken off from phase separator 20.

Figure 7:
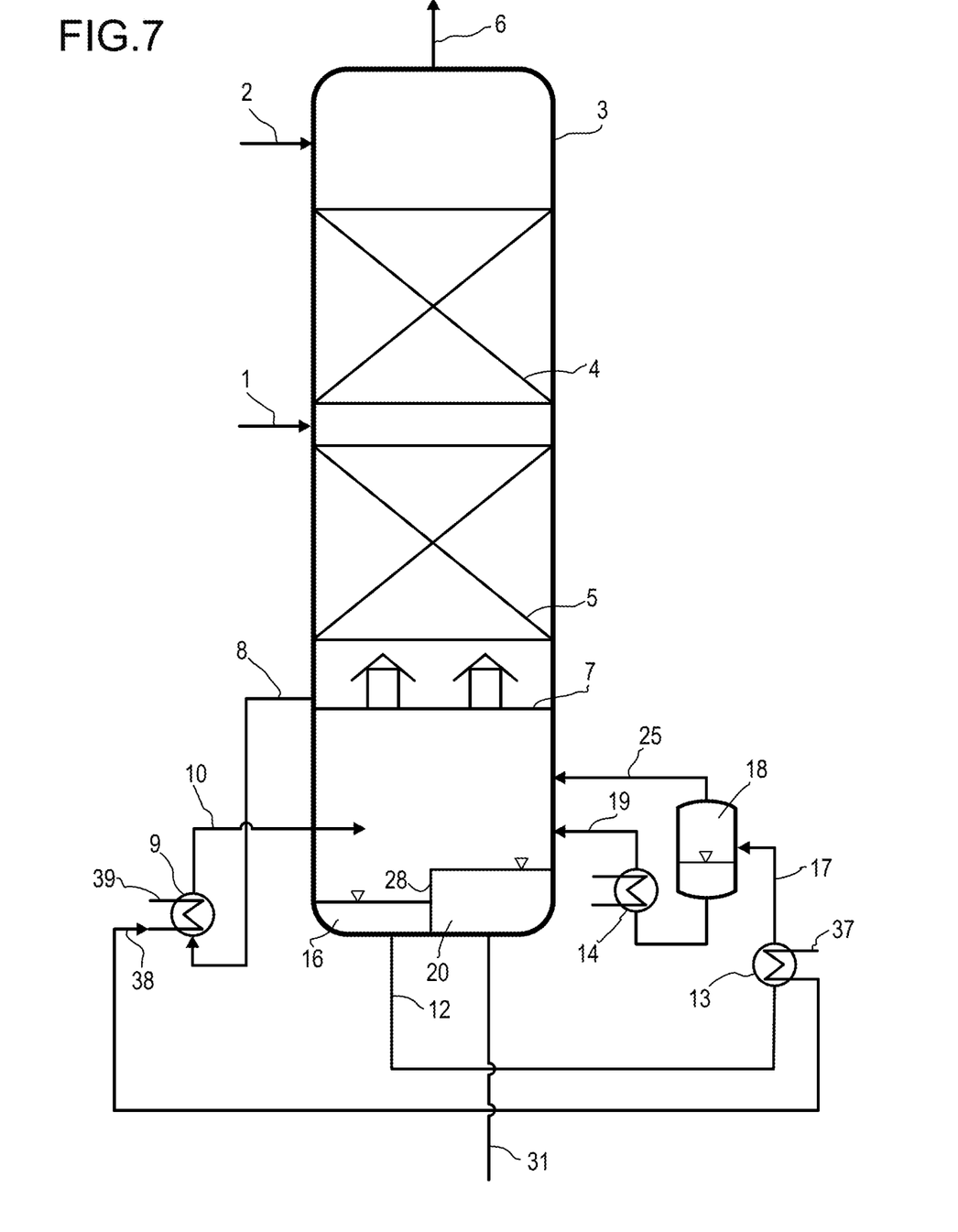

In the embodiment of column 3 shown in FIG. 7, the first cell 16 and the third cell 20 are integrated into the sump of the column. The second cell 18 is a phase separator arranged outside the column. The two-phase mixture formed from the liquid fraction in the first heat exchanger 9 is conducted via line 10 into the region above the first cell 16 situated between the sump and the collecting tray 7 in such a manner that the non-evaporated proportion of the liquid fraction collects as sump fraction in the first cell 16 and the resultant vapor is released into the column 3. The sump fraction is taken off from the first cell 16 via line 12 and is conducted through the second heat exchanger 13 and via line 17 into the phase separator 18. The sump fraction is taken off from the phase separator 18 and conducted through the third heat exchanger 14 and via line 19 into the region above the third cell 20 situated between the sump and the collecting tray 7 in such a manner that the non-evaporated proportion of the sump fraction collects in the third cell 20. The vapor collecting in the phase separator is released into the column via line 25. The sump fraction to be fed to the stripper via line 31 is taken off from the third cell 20.

Figure 8:
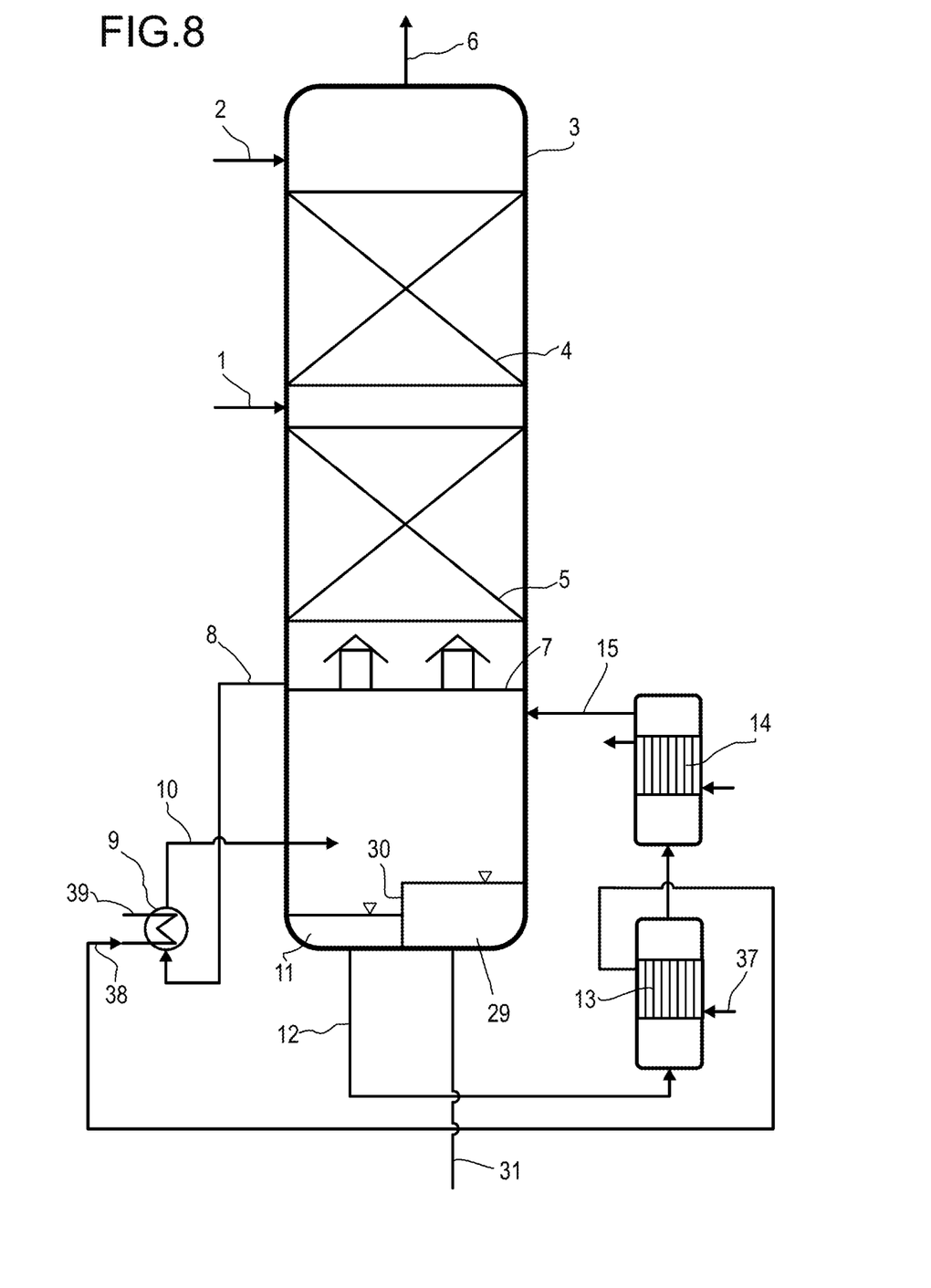
Figure 9:
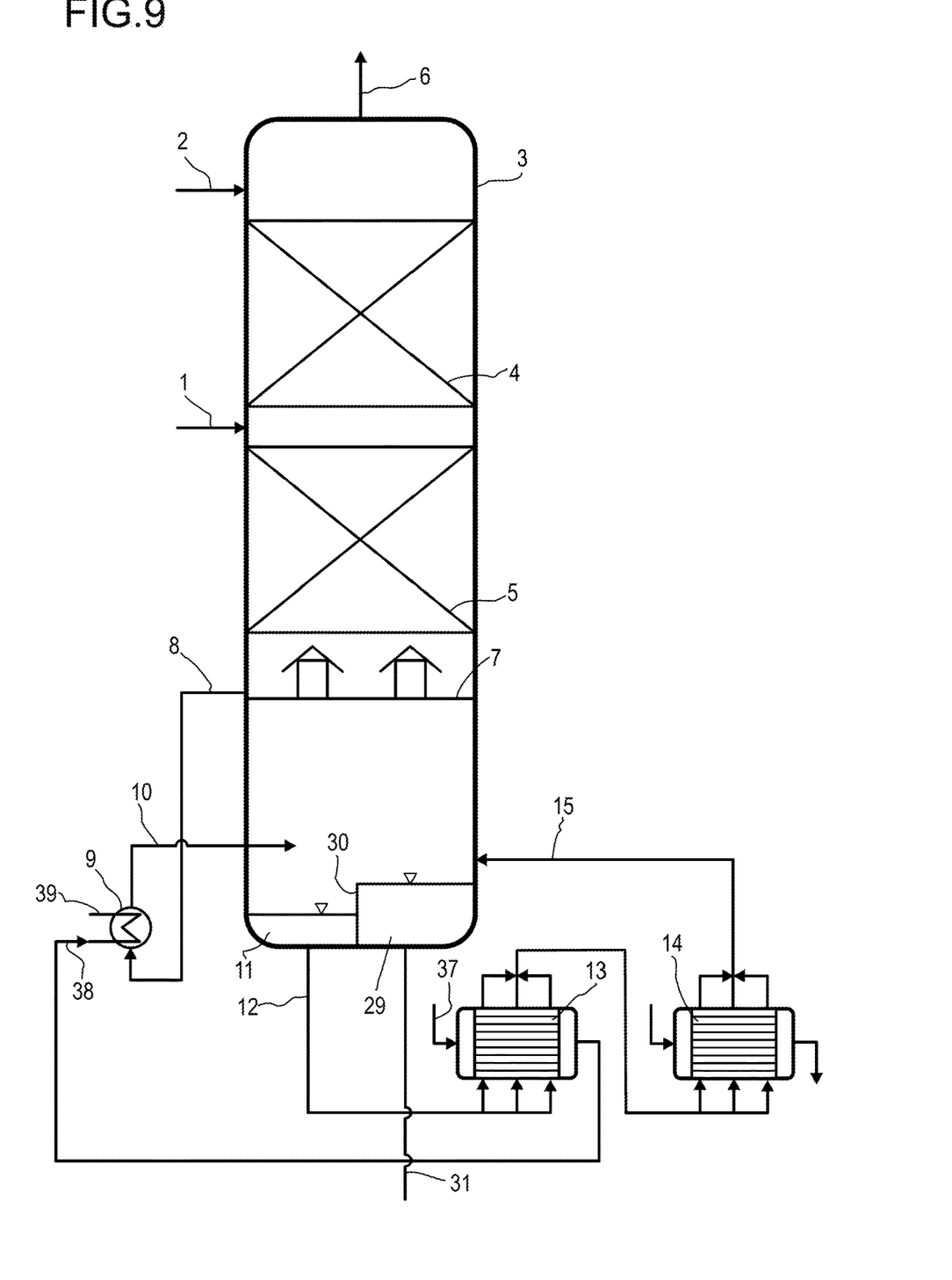

The embodiments of column 3 shown in FIGS. 8 and 9 permit a procedure in which the sump fraction is circulated via a sump circulation in which the sump fraction is conducted successively through the second indirect heat exchanger and the third indirect heat exchanger and the circulated sump fraction, after the third indirect heat exchanger, is conducted via a cell that is integrated into the sump of the column and thereby communicating with the column on the vapor side.

In the embodiment of the column 3 shown in FIG. 8, the two-phase mixture is conducted via line 10 into the region of the column 3 situated between the sump and the collecting tray 7 in such a manner that the non-evaporated proportion of the liquid fraction collects as sump fraction 11 and the resultant vapor is released into the column 3. The sump fraction 11 is circulated via a sump circulation in which the sump fraction is taken off from the sump of the column via line 12 and conducted successively through the second indirect heat exchanger 13 and the third indirect heat exchanger 14 and via line 15 into the region above the cell 29 situated between the sump and the collecting tray 7, in such a manner that the non-evaporated proportion of the sump fraction collects in the cell 29. The sump fraction to be fed to the stripper via line 31 is taken off from the cell 29. The two heat exchangers 13 and 14 are vertically oriented tube-bundle heat exchangers arranged one above the other.

The embodiment of the column shown in FIG. 9 differs from the embodiment shown in FIG. 8 in that the two heat exchangers 13 and 14 are horizontally orientated tube-bundle heat exchangers one beside the other.

The invention claimed is:

1. A method for separating a mixture of a material A and a material B by extractive distillation, using an extraction medium having a higher affinity to B than to A, wherein the method comprises:
   a) conducting a feed stream comprising A and B towards the extraction medium in a column, wherein an overhead fraction comprising A, and also a liquid fraction comprising B and extraction medium, are obtained,
   b) collecting the liquid fraction on a collecting tray and heating and partially evaporating the liquid fraction in a first indirect heat exchanger, where a first resultant vapor is released into the column and a non-evaporated proportion of the liquid fraction is collected as a sump fraction in a sump of the column,
   c) successively heating the sump fraction in a second indirect heat exchanger and a third indirect heat exchanger and in part evaporating the sump fraction, wherein a second resultant vapor is at least in part released into the column,
   d) separating the sump fraction in a stripper, into: i) a fraction comprising B and ii) an extraction medium fraction,
   e) using the extraction medium fraction as a heating medium for the second indirect heat exchanger, wherein a partially cooled extraction medium fraction is obtained, and an external heating medium is used for the third indirect heat exchanger, and
   f) using the partially cooled extraction medium fraction as a heating medium for the first indirect heat exchanger.

2. The method according to claim 1, wherein the sump fraction is successively conducted through the second indirect heat exchanger and the third indirect heat exchanger.

3. The method according to claim 2, wherein, downstream of the third heat exchanger, a circulated sump fraction is conducted through a cell, communicating a vapor side with the column, where in the cell a resultant vapor is separated off from the sump fraction, and a vapor is separated from the sump fraction.

4. The method according to claim 3, wherein the cell is integrated into the sump of the column, or is a phase separator arranged outside the column.

5. The method according to claim 1, wherein the sump fraction is conducted through three cells, each communicating with a vapor side with the column, by collecting the sump fraction in a first cell integrated into the sump of the column, taking off the sump fraction from the first cell and conducting it through the second indirect heat exchanger into a second cell, taking off the sump fraction from the second cell and conducting it through the third indirect heat exchanger into a third cell and taking off from the third cell the sump fraction that is to be fed to the stripper.

6. The method according to claim 5, wherein the three cells are integrated into the sump of the column.

7. The method according to claim 5, wherein the third cell is a phase separator arranged outside the column.

8. The method according to claim 5, wherein the second cell is a phase separator arranged outside the column.

9. The method according to claim 1, wherein the first indirect heat exchanger is a natural-circulation evaporator.

10. The method according to an claim 1, wherein
   i. A is butane and B is butene, butadiene or a mixture thereof, or
   ii. A is pentane and B is pentene, isoprene or a mixture thereof, or
   iii. A is hexane and B is benzene, or
   iv. A is 2-propanol and B is water, or
   v. A is hydrogen chloride and B is water, or
   vi. A is acetonitrile and B is water, or
   vii. A is 2-butyl acetate and B is 2-butanol, or
   viii. A is tetrahydrofuran and B is methanol, or
   ix. A is acetone and B is chloroform, or
   x. A is ethanol and B is water, or
   xi. A is acetone and B is methanol, or
   xii. A is a mixture of ethanol and water and B is ethyl acetate.

11. The method according to claim 10, wherein the extraction medium comprises, in the case of
   i. dimethylformamide, N-methylpyrrolidone, acetonitrile, furfural, or dimethyl sulfoxide,
   ii. dimethylformamide or N-methylpyrrolidone,
   iii. phenol, N-methylpyrrolidone, or N-formylmorpholine,
   iv. a solution of calcium chloride in water, dimethyl sulfoxide, or ethylene glycol,
   v. sulfuric acid,
   vi. ethylene glycol,
   vii. N,N-dimethylacetamide,
   viii. water,
   ix. dimethyl sulfoxide,
   x. ethylene glycol, glycerol, or dimethyl sulfoxide,
   xi. water,
   xii. dimethyl sulfoxide, glycerol, diethylene glycol, 1-naphthol, hydroquinone, or dimethylformamide.

12. The method according to claim 1, wherein A is butane and B is butene, butadiene or mixtures thereof, and the extraction medium comprises N-methylpyrrolidone.

* * * * *

UNITED STATES PATENT AND TRADEMARK OFFICE
CERTIFICATE OF CORRECTION

Page 1 of 1

PATENT NO.        : 10,793,494 B2
APPLICATION NO.   : 16/072695
DATED             : October 6, 2020
INVENTOR(S)       : Asprion It is certified that error appears in the above-identified patent and that said Letters Patent is hereby corrected as shown below:

In the Claims

In Column 12, Claim 3, Lines 49-50, "the the" should read -- the --.

In Column 13, Claim 10, Line 5, "an claim" should read -- claim --.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*